US005760239A

United States Patent [19]

Wu

[11] Patent Number: 5,760,239
[45] Date of Patent: Jun. 2, 1998

[54] PROCESS FOR THE MANUFACTURE OF 5-(ALKOXYMETHYL)PYRIDINE-2,3-DICARBOXYLATE SALT

[75] Inventor: Wen-Xue Wu, Lawrenceville, N.J.

[73] Assignee: American Cyanamid Company, Madison, N.J.

[21] Appl. No.: 895,489

[22] Filed: Jul. 16, 1997

Related U.S. Application Data

[63] Continuation of Ser. No. 464,905, Jun. 5, 1995, abandoned.
[51] Int. Cl.$^6$ .................. C07D 213/61; C07D 213/803; C07D 213/84
[52] U.S. Cl. .................. 546/286; 546/310; 546/321
[58] Field of Search .................. 546/286, 310, 546/321

[56] References Cited

U.S. PATENT DOCUMENTS 5,288,866  2/1994  Strong .................. 544/215
5,334,576  8/1994  Doehner, Jr. et al. .................. 504/128
5,378,843  1/1995  Strong .................. 544/215

FOREIGN PATENT DOCUMENTS 7-10794  1/1995  Japan .

*Primary Examiner*—Mukund J. Shah
*Assistant Examiner*—Ann M. Kessinger
*Attorney, Agent, or Firm*—Barbara L. Renda

[57] ABSTRACT

There is provided an improved method for the conversion of 5,6-dicarboxyl-3-pyridylmethyl ammonium halide to 5-(alkoxymethyl)pyridine-2,3-dicarboxylate salt via a single step closed reaction with the appropriate alcohol and a base at a temperature of about 120°–180° C.

The product pyridinedicarboxylate salt is an important intermediate in the manufacture of pyridine imidazolinone herbicidal agents.

12 Claims, No Drawings

PROCESS FOR THE MANUFACTURE OF 5-(ALKOXYMETHYL)PYRIDINE-2,3-DICARBOXYLATE SALT

This is a continuation of application Ser. No. 08/464,905 filed on Jun. 5, 1995, now abandoned.

BACKGROUND OF THE INVENTION

The discovery of the imidazolinone herbicides in the 1970's has led to the development of a number of world-class herbicidal products. Because of their versatility, low toxicicity and environmental safety, these products are used in many different crops and play a vital role in the production of food and fiber throughout the world. Due to the importance of the imidazolinones in weed control in agriculture a great deal of research continues to be conducted to improve and broaden crop selectivity, to enhance grass weed control and to extend crop rotational profile. As a result, compounds such as 5-(and/or 6)substituted 2-(2-imidazolin-2-yl)nicotinates and methods for the preparation thereof are of increasing importance.

The use of 5,6-dicarboxyl-3-pyridylmethyl ammonium halide compounds to prepare 5-(substituted pyridine-2,3-dicarboxylate intermediates in the imidazolinone process of manufacture is described in U.S. Pat. No. 5,378,843 and U.S. Pat. No. 5,288,866. The process so described is a 3-step conversion of the starting methylammonium halide to the corresponding alkoxyalkyl- or alkylthioalkylpyridine diacid intermediate.

It is an object of this invention to provide an improved process for the preparation of 5-(alkoxymethyl)pyridine-2,3-dicarboxylate salt in a single step from the appropriate 5,6-dicarboxylic-3-pyridylmethylammonium halide precursor.

It is another object of this invention to provide a ready and convenient source of an important intermediate in the manufacture of imidazolinone herbicides.

It is a feature of this invention that said intermediate is obtained in excellent yield and good purity.

Further objects and features of the invention will become apparent from the detailed description set forth below.

SUMMARY OF THE INVENTION

The present invention provides a simple and effective process for the manufacture of the 5-(alkoxymethyl)pyridine-2,3-dicarboxylate salt of formula I

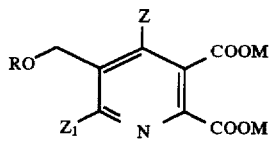

wherein Z is hydrogen or halogen;

$Z_1$ is hydrogen, halogen, cyano or nitro;

R is $C_1$–$C_4$alkyl optionally substituted with phenyl which is optionally substituted with one to three halogen or $C_1$–$C_4$alkyl groups or phenyl optionally substituted with one to three halogen or $C_1$–$C_4$alkyl groups; and M is an alkaline metal or an alkaline earth metal which comprises reacting a compound of formula II

wherein Z and $Z_1$ are as described above for formula I;

Y and $Y_1$ are each independently OH, ONa, OK or $OC_1$–$C_4$alkyl;

X is Cl, Br, I or $R_1SO_3$;

$R_1$ is $C_1$–$C_4$alkyl or phenyl optionally substituted with one to three halogen, nitro, cyano, $C_1$–$C_4$alkyl or $C_1$–$C_4$alkoxy groups;

Q is

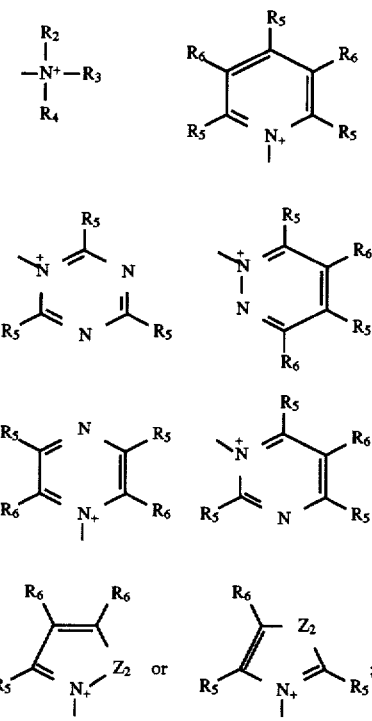

$R_2$, $R_3$ and $R_4$ are each independently $C_1$–$C_8$alkyl, and when taken together, $R_2$ and $R_3$ may form a 5- or 6-membered ring optionally interrupted by O, S or $NR_6$;

$Z_2$ is O, S or $NR_7$;

$R_7$ is $C_1$–$C_4$alkyl; and $R_5$ and $R_6$ are each independently hydrogen, halogen, $C_1$–$C_4$ alkyl or $C_1$–$C_4$alkoxy, and when taken together, $R_5$ and $R_6$ may form a 5- or 6-membered ring optionally interrupted by O, S, or $NR_7$ and optionally substituted with one to three halogen, $C_1$–$C_4$alkyl, or $C_1$–$C_4$ alkoxy groups with a base in the presence of an alcohol, ROH, wherein R is as described above for formula I at a temperature of about 120° to 180° C. under pressure in a closed system.

The formula I salts are readily converted to the corresponding diacids in aqueous acid media.

DETAILED DESCRIPTION OF THE INVENTION

Under actual manufacturing conditions, frequently anhydrous conditions may be difficult to maintain, either because aqueous reagents or aqueous solvents are more effective, more economic or more readily available or because water is inadvertantly introduced into an anhydrous system via contaminated reaction vessels, pipelines, solvent sources or the like. Methylammonium halide-5,6-pyridine anhydrides, thioanhydrides, imides, diesters and diamides are all susceptible to hydrolysis to the corresponding diacids or dicarboxylate salts in the presence of water and base. The conversion of all of the above-said methylammonium halide pyridines to their corresponding alkoxymethylpyridine diacids is described in U.S. Pat. No. 5,378,843. However, optimum reaction yields and product purity are obtained when the starting substrate is a methylammonium halide-5, 6-pyridine anhydride, thioanhydride, imide, diester or diamide. Corresponding pyridine diacids or dicarboxylate salts give poor conversion products with low yields and products contaminated with the unconverted methylammmonium halide pyridine diacid side-product.

It has now been found, methylammonium halide-5, 6pyridine diacids or dicarboxylates of formula II may be readily and effectively converted to the corresponding formula I alkoxyalkylpyridine dicarboxylate salt via a single step closed reaction with the appropriate alcohol in the presence of a base at a temperature of about 120° C.–180° C., preferably about 120°–150° C.

Manufacturing procedures may also be non-anhydrous in view of the hygroscopic properties of the diester methylammonium salts of formula IIa. Hygroscopic starting materials almost ensure the unavoidable introduction of water into a manufacturing process. Therefore, the inventive method would be especially useful in avoiding lowered yields and purity due to product mixtures such as that shown in flow diagram I, i.e., the mixture of compounds of formula I and formula IIb.

Flow Diagram I, shown below, illustrates the above-discussed reactions, wherein, for purposes of illustration, the starting methylammonium halide pyridine substrate is a dimethyl ester and water is assumed to be present in either step 1 or step 2.

FLOW DIAGRAM I

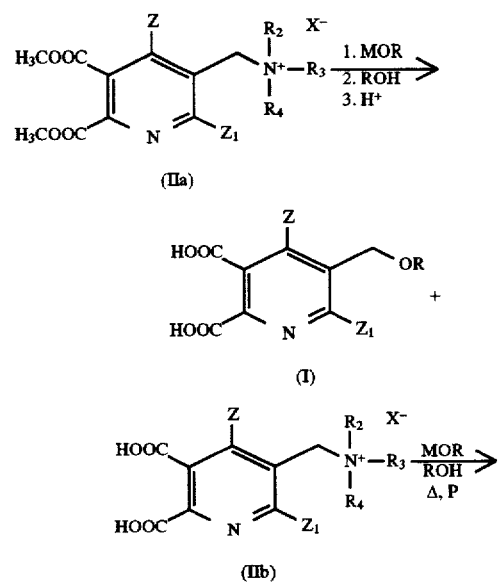

-continued
FLOW DIAGRAM I

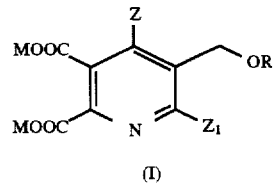

(I)

In addition to enabling conversion of unconverted methylammonium halide pyridine diacids to the desired alkoxymethyl products, advantageously the present method of invention may also be used to directly and effectively convert the starting methylammonium halide pyridine diester, in a single step, to the desired alkoxymethyl dicarboxylate salt product as shown in flow diagram II.

FLOW DIAGRAM II

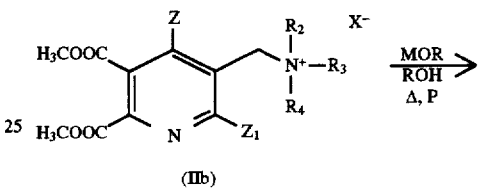

(IIb)

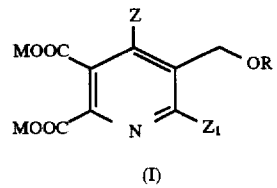

(I)

Bases suitable for use in the method of invention are alkaline metal or alkaline earth metal hydrides, hydroxides, carbonates or $C_1$–$C_4$alkoxides, preferably sodium or potassium hydroxide or alkoxide. Suitable alkaline metals are sodium or potassium. Suitable alkaline earth metals are calcium, magnesium and the like. Alkaline metals such as sodium or potassium are preferred.

Suitable reaction temperatures are about 120° to 180° C., preferably about 120° to 150° C. Reaction pressures would be those pressures which normally accompany heating a solvent in a closed reaction system to a temperature range above its boiling point.

The product formula I alkoxymethylpyridine dicarboxylates are important intermediates in the preparation of imidazolinone herbicides. Said herbicides and exemplary methods of ther preparation which utilize the formula I intermediates or the corresponding free acids thereof are described in U.S. Pat. No. 5,334,576.

In order to present a more clear understanding of the invention, specific examples thereof are set forth below. These examples are merely illustrative and are not to be understood as limiting the scope and underlying principles of the invention in any way. Indeed, various modifications of the invention, in addition to those shown and described herein, will become apparent to those skilled in the art from the following examples and the foregoing description. Such modifications are also intended to fall within the scope of the appended claims. The term, LC, designates liquid chromatography.

EXAMPLE 1

Preparation of disodium 5-(methoxymethyl)pyridine-2,3-dicarboxylate from disodium [5,6-(dicarboxylate-3-pyridyl)

methyl]trimethylammonium bromide

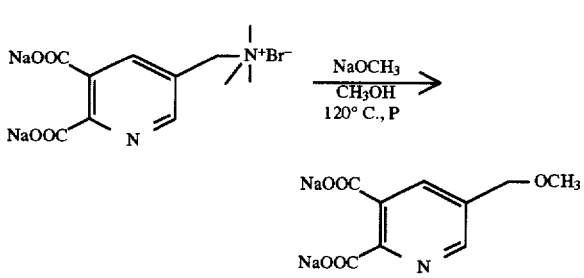

A mixture of disodium [(5,6-dicarboxylate-3-pyridyl) methyl]trimethylammonium bromide (5.0 g, 13.8 mmol) and a 25% wt/wt solution of sodium methoxide in methanol (4.46 g, 20.7 mmol of NaOCH₃) in 75 g of methanol is heated at 120° C. for 21 hours in a pressure reactor. The reaction is cooled to room temperature, treated with water and concentrated to a final weight of 55.03 g. A 5.0 g sample is assayed by LC analysis (30% CH₃CN, 0.77M H₃PO₄). The remainder of the reaction solution is evaporated to dryness to give a solid residue, identified by NMR analysis.

The above analyses show the title product is present in 80% yield and 0.3% of the starting material is recovered.

EXAMPLE 2

Evaluation of the displacement of trimethylammonium bromide with methoxide

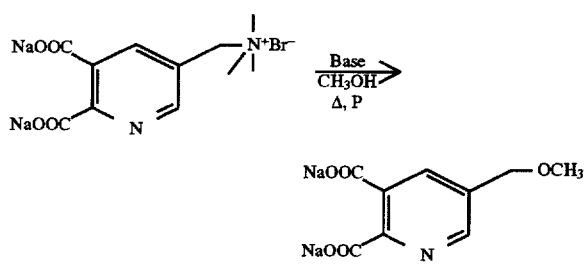

Using essentially the same procedure described in Example I above and varying the reaction temperature and base, the product yields and recovered starting material are observed and recorded in Table I.

TABLE I

| Temperature | Base | Product % Yield | Starting Material % Recovered |
| --- | --- | --- | --- |
| 150° C. | NaOCH₃ | 76% | 0% |
| 100° C. | NaOCH₃ | 46% | 39% |
| 120° C. | K₂CO₃ | 62% | 30% |

EXAMPLE 3

Comparative evaluation of the conversion of a mixture of [(5,6-diester(and 5,6-diacid)-3-pyridylmethyl)] trimethylammonium bromide to 5-(methoxymethyl)-pyridine-2,3-dicarboxylic acid in the presence of water

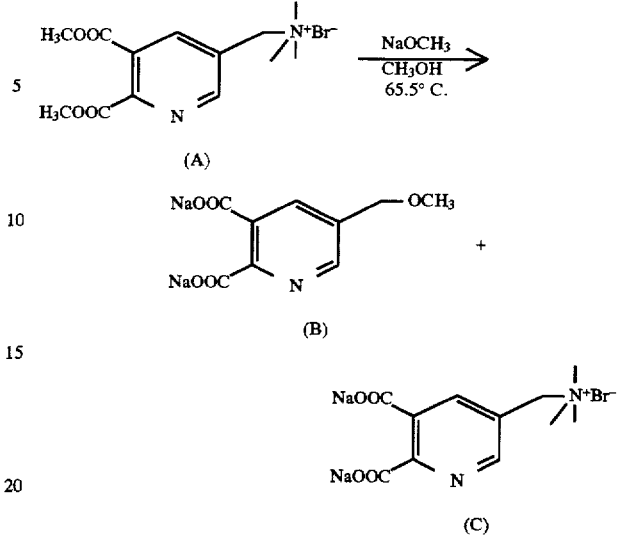

A mixture of 5.0 g of 95.5% pure dimethyl [(5,6-dicarboxylate-3-pyridyl)methyl]trimethylammonium bromide, which has been stored and is known to contain some water due to its hygroscopic properties, and 4.36 g of a 25% wt/wt solution of sodium methoxide in methanol (20 mmol of NaOCH₃) in 50 g of methanol is heated at reflux temperature for 5 hours, treated with 23 g of 50% aqueous sodium hydroxide (2 equiv. of NaOH) and 20 mL of water, continued to heat at reflux temperature for 2 hours, and cooled to room temperature. The resultant reaction mixture is concentrated to a weight of 55.14 g and a log sample is assayed by LC analysis. The analysis is shown below.

| Compound | % Concentration | % Real Yield |
| --- | --- | --- |
| B | 4.51% | 82% |
| C | 0.83% | 10% |

As can be seen from the results above, if water is present along with the 5,6-diester-3-pyridylmethylammonium halide starting material, the reaction products will be the corresponding methoxymethylpyridine product along with the pyridylmethylammonium halide dicarboxylate side-product, under refluxing methanol conditions.

EXAMPLE 4

Comparative evaluation of the conversion of disodium 5,6-[(dicarboxylate-3-pyridyl)methyl]trimethylammonium bromide to disodium 5-(methoxymethyl)pyridine-2,3-dicarboxylate acid in refluxing methanol

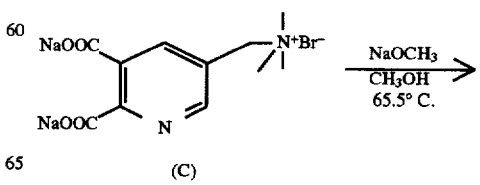

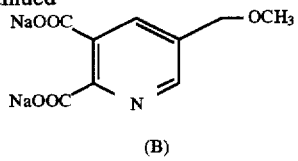

(B)

A mixture of disodium [(5,6-dicarboxylate-3-pyridyl)methyl]trimethylammonium bromide (5.0 g, 13.8 mmol) and 4.46 g of a 25% wt/wt methanolic solution of sodium methoxide (20.7 mmol of NaOCH₃) in 40 g of methanol is heated at reflux temperatures for 8 days, cooled to room temperature, treated with water and concentrated in vacuo. The resultant reaction mixture is assayed by LC analyses using 30% CH₃CN in 0.77M H₃PO₄ and also using 0.78% isopropanol in 0.05M H₃PO₄. The results obtained are shown below.

| Assay | Compound | % yield |
|---|---|---|
| 30% CH₃CN, | B | 29% |
| 0.77M H₃PO₄ | C | 67% |
| 0.78% iprOH, | B | 33% |
| .05M H₃PO₄ | C | 65% |

As can be seen from the data shown above, conversion of the starting disodium salt C to the desired product B is incomplete after 8 days under refluxing methanol conditions.

I claim:

1. A process for the preparation of a compound of formula I

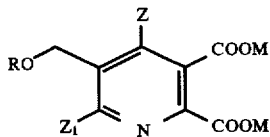

wherein Z is hydrogen or halogen;

$Z_1$ is hydrogen, halogen, cyano or nitro;

R is $C_1$–$C_4$alkyl optionally substituted with phenyl which is optionally substituted with one to three halogen or $C_1$–$C_4$alkyl groups or phenyl optionally substituted with one to three halogen or $C_1$–$C_4$alkyl groups; and M is an alkaline metal or an alkaline earth metal which comprises reacting a compound of formula II

wherein Z and $Z_1$ are as described above for formula I;

Y and $Y_1$ are each independently OH, ONa, OK or $OC_1$–$C_4$alkyl;

X is Cl, Br, I or $R_1SO_3$;

$R_1$ is $C_1$–$C_4$alkyl or phenyl optionally substituted with one to three halogen, nitro, cyano, $C_1$–$C_4$alkyl or $C_1$–$C_4$alkoxy groups;

Q is

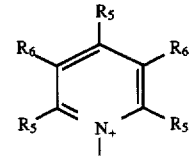

$R_2$, $R_3$ and $R_4$ are each independently $C_1$–$C_8$alkyl, and when taken together, $R_2$ and $R_3$ may form a 5- or 6-membered ring optionally interrupted by O, S or $NR_6$;

$Z_2$ is O, S or $NR_7$;

$R_7$ is $C_1$–$C_4$alkyl; and $R_5$ and $R_6$ are each independently hydrogen, halogen, $C_1$–$C_4$ alkyl or $C_1$–$C_4$alkoxy, and when taken together, $R_5$ and $R_6$ may form a 5- or 6-membered ring optionally interrupted by O, S, or $NR_7$ and optionally substituted with one to three halogen, $C_1$–$C_4$alkyl, or $C_1$–$C_4$alkoxy groups with a base in the presence of an alcohol, ROH, wherein R is as described above for formula I at a temperature of about 120° to 180° C. under pressure in a closed system wherein the base is an alkaline metal or alkaline earth metal hydride, $C_1$–$C_4$ alkoxide, hydroxide, or carbonate.

2. The process according to claim 1 wherein R is $C_1$–$C_4$alkyl.

3. The process according to claim 1 wherein Q is

4. The process according to claim 1 wherein the temperature is about 120° C. to 150° C.

5. The process according to claim 3 wherein $R_2$, $R_3$ and $R_4$ are each independently $C_1$–$C_4$alkyl.

6. The process according to claim 3 wherein X is Br.

7. The process according to claim 1 wherein the base is sodium hydroxide or sodium methoxide and R is methyl.

8. The process according to claim 7 wherein the temperature is 120° C. to 150° C.

9. The process according to claim 8 wherein Q is trimethylammonium and X is Br.

10. The process according to claim 3 wherein Y is ONa or OCH$_3$.

11. The process according to claim 10 wherein the base is sodium or potassium hydroxide or C$_1$–C$_4$ alkoxide.

12. The process according to clam 10 wherein the base is NaOCH$_3$ or K$_2$CO$_3$.

* * * * *